United States Patent [19]

Kimble

[11] 4,292,042
[45] Sep. 29, 1981

[54] ANALYSIS OF VINYL ACETATE

[75] Inventor: Howard J. Kimble, Scott Depot, W. Va.

[73] Assignee: Union Carbide Corporation, New York, N.Y.

[21] Appl. No.: 149,732

[22] Filed: May 14, 1980

[51] Int. Cl.³ .................... G01N 1/22; G01N 31/08
[52] U.S. Cl. ............................. 23/232 R; 23/232 C
[58] Field of Search ............ 23/230 M, 232 R, 232 C; 422/83, 88, 89; 73/23

[56] References Cited

U.S. PATENT DOCUMENTS

| | | |
|---|---|---|
| 1,614,615 | 1/1927 | Jannick et al. |
| 2,694,923 | 11/1954 | Carpenter ............................ 73/23 |
| 3,102,192 | 8/1963 | Skala .............................. 23/232 R X |
| 3,636,087 | 1/1972 | Caserio, Jr. |
| 3,691,251 | 9/1972 | Bauer. |

FOREIGN PATENT DOCUMENTS 672563  7/1979  U.S.S.R. ............................ 23/232 C

OTHER PUBLICATIONS

Bianchi et al., Chemical Abstracts, vol. 89, 1978, No. 89: 11150n.

Primary Examiner—Arnold Turk
Attorney, Agent, or Firm—Bernard F. Crowe

[57] ABSTRACT

Vinyl acetate in ambient air is measured by first drying the air sample, then adsorbing the vinyl acetate on an adsorbent containing a polymerization inhibitor, followed by desorption and assay of the desorbed vinyl acetate.

7 Claims, 1 Drawing Figure

U.S. Patent
Sep. 29, 1981
4,292,042
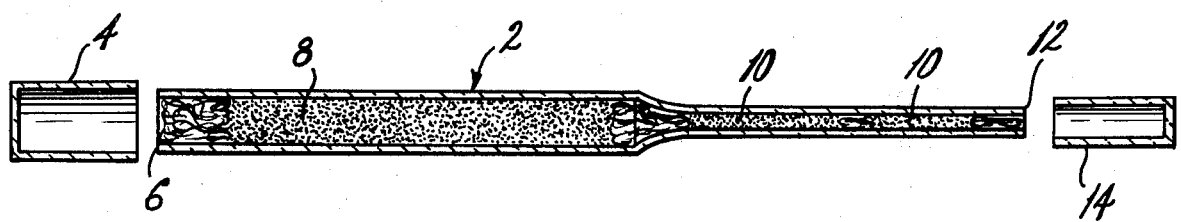

ANALYSIS OF VINYL ACETATE

BACKGROUND OF THE INVENTION

This invention pertains to a method of assaying vinyl acetate and more particularly to an assay of vinyl acetate in ambient air.

Environmental restrictions and regulations relating to the presence of chemicals in the ambient air present in plant and other working areas are particularly stringent with respect to monomeric materials. A need arose therefore for means of monitoring the levels of widely used monomers, such as, vinyl acetate which is used in a plethora of polymeric materials.

One of the difficulties associated with taking routine assays of vinyl acetate in ambient air present in industrial polymerization plants is the fact that it hydrolyzes with water to form acetic acid and vinyl alcohol. The latter immediately undergoes a rearrangement to acetaldehyde. Furthermore, upon vaporization from the liquid state, vinyl acetate loses any polymerization inhibitor which was present in the liquid vinyl acetate. This makes any analytical procedure more difficult since vinyl acetate which polymerizes will not appear in the final analysis as a monomer. It is common to inhibit vinyl acetate liquid with from 5 to about 20 parts per million of a free radical stabilizer, such as, hydroquinone. The boiling point of hydroquinone is far too high to permit its evaporation with vinyl acetate to the vapor state. The problem of analyzing ambient air to which employees in a vinyl acetate polymerization plant are exposed is therefore made inaccurate because of the hydrolysis or polymerization of vinyl acetate after collection of a representative air sample prior to analysis.

It is therefore an object of this invention to provide a facile method of determining the vinyl acetate monomer levels in random ambient air samples collected in a working vinyl acetate plant during the time of worker exposure to this monomer.

SUMMARY OF THE INVENTION

A method of measuring the amount of vinyl acetate monomer in an ambient air atmosphere has been discovered which comprises the series of steps of:

(A) contacting a measured volume of ambient air containing vinyl acetate monomer vapor with drying means thereby freeing said measured volume of ambient air of water vapor;

(B) contacting said water vapor-freed measured volume of ambient air with vinyl acetate adsorbing means, said adsorbing means containing an inhibitor for vinyl acetate polymerization thereby separating the vinyl acetate monomer in the measured volume of ambient air from said ambient air;

(C) desorbing the adosrbed vinyl acetate monomer from said vinyl acetate adsorbing means; and (D) measuring the amount of desorbed vinyl acetate monomer with analytical means for assaying vinyl acetate monomer.

Various known drying agents can be used as the drying means in the instant invention. They include anhydrous calcium sulfate (sold under the Trademark Drierite by W. A. Hammond Drierite Company, Xenia, Ohio), crystalline zeolites of the molecular sieve type having pore dimensions large enough to permit passage of water molecules, magnesium chloride, magnesium sulfate, and the like.

Suitable vinyl acetate monomer adsorbents include activated carbon, bead activated carbon, activated charcoal, organic porous polymers or resins, such as, crosslinked poly(n-glycidyl-piperazine), blown or expanded polysulfone resins and the like. The preferred adsorbents are bead activated carbon and activated carbon derived from petroleum.

The choice of vinyl acetate monomer polymerization inhibitors is not critical and thus includes in addition to hydroquinone already mentioned, the monomethyl ether of hydroquinone, 2,6-ditertiarybutylp-cresol, phenyl-beta-naphthylamine, catechol, t-butylcatechol, asobisisobutyronitrile, and the like.

The combination of drying and adsorbing means may be conveniently mounted in a glass sampling tube wherein the drying means would constitute the front of the tube and be separated by glass wool or some other inert material from a second compartment connected in the series to the first containing the adsorbing material.

A sampling tube utilizing the concepts of the invention is shown in the FIGURE.

2 is a glass sampling tube.

4 is a combination of cap and plug for sealing off one end of sampling tube (2).

6 is an orifice into which ambient air is drawn by vacuum.

8 is a section of tube (2) packed with 2 grams of a drying agent.

10 are sections in tube (2) filled with a vinyl acetate adsorbent and polymerization inhibitor, the first being the primary section containing 150 mg. of inhibited adsorbent and the second being a backup section containing 75 mg. of inhibited adsorbent.

12 is the other end of tube (2) to which a vacuum is applied to draw air into the tube to be sampled.

14 is a combination cap and plug for the other end of sampling tube (2).

The size and configuration of the sampling tube is not critical the only limit being that it be sufficiently large to obtain enough vinyl acetate monomer to be assayed conveniently.

DESCRIPTION OF THE INVENTION

Sampling of ambient air for vinyl acetate monomer content can be carried out as follows: (a) Immediately before sampling remove the cap plugs.

(b) Attach the sampling tube to a portable personnel pump with the backup section next to the pump.

(c) For long term sampling set the air flow rate through the sampling tube from 50 cc's to 100 cc's per minute.

(d) For short term sampling flow rates of up to one liter per minute can be used to collect sufficient quantities of vinyl acetate to measure quantitively.

(e) If a personnel sample is to be taken, put the tube in an appropriate holder to protect the individual from the glass tube.

(f) A total of 15–48 liters for personnel and 15–90 liters for short term exposure limit samples of air should be sampled at a flow rate of 50–1000 cc of air per minute. Record the temperature and the barometric pressure at the sampling site. Record the total liters of air pulled through the tube.

(g) Cap the ends of the sampling tube with the ca-plugs which can be suitably fabricated from polyethylene and save the tubes for analysis. Sampling tubes should be kept refrigerated unless they are analyzed within five days of sampling.

(h) A sampling tube identical to the above-described one should be preserved with no air pulled through it to serve as a blank.

ANALYTICAL PROCEDURE

Analysis of the vinyl acetate adsorbed in the sampling tube is carried out as follows:

(a) Remove the plug from the back or carbon section of the sampling tube.

(b) Remove the glass wool retainer plug and discard. Take care that no adsorbent particles are removed with the glass wool.

(c) Transfer the adsorbent from the primary section and backup section of the tube into separate desorption vials. Cool in wet ice for 5 minutes while capped.

(d) Pipet 2 ml of acetone into 98 ml of carbon disulfide and mix well. Pipet 1.0 ml of this solvent into each desorption vial and cap securely.

(e) Sonify for 5 minutes at ambient temperature or shake on the Burrel shaker for 15 minutes. Do not allow to stand more than 90 minutes before analyzing. The vials should be shaken vigorously to desorb the vinyl acetate, if no mechanical device is used.

(f) Solvent flush injection technique. This injection technique is designed to eliminate difficulties arising from blow-back or distillation with the needle of the microliter syringe.

(g) Flush a 10-$\mu$l syringe with $CS_2$-acetone several times to wet the barrel and plunger.

(h) Draw 1-$\mu$l of $CS_2$-acetone into the syringe and remove the tip of the needle from the solvent. Withdraw the plunger an additional 0.5 $\mu$l to separate the $CS_2$-acetone from the sample with a pocket of air.

(i) Dip the needle into the sample solution in the desorption vial and withdraw the plunger until the air bubble between the solvent and the sample has passed the 2-$\mu$l mark on the syringe.

(j) Remove the top of the needle from the sample solution and adjust the volume in the syringe until the meniscus of the air bubble rests on the 2-$\mu$l mark. Remove the excess sample solution from the tip of the needle.

(k) Pull the plunger back an additional 0.5 $\mu$l to prevent the sample solution from evaporating from the tip of the needle.

(l) Inject the entire contents of the syringe into a chromatographic analysis apparatus.

(m) Measure the peak area or height and determine the organic content from a previously prepared calibration curve.

(n) Analyze the backup (small) section of activated carbon tube in the same manner as the primary.

CALIBRATION CURVE (a) By means of a microliter syringe, inject 10.0$\mu$l of vinyl acetate into a 10-ml volumetric flask containing the carbon disulfide-2 percent acetone desorption solvent. Dilute to the mark with additional $CS_2$-acetone. This solution contains 928 $\mu$g of vinyl acetate per ml.

(b) Pipet .25, 0.5, 1, 2, and 4-ml aliquots of the 928 $\mu$g per ml solution into respective 10-ml volumetric flasks and dilute to the mark with $CS_2$-acetone. These solutions contain 23.2, 46.4, 92.8, 185.6, 371.2 $\mu$g per ml of vinyl acetate respectively.

(c) Inject these standards into the chromatograph using the procedure described in the Analytical Procedure, paragraphs f through l.

(d) Plot peak height or area versus micrograms of vinyl acetate per ml.

DESORPTION EFFICIENCY (a) The desorption efficiency (percentage of the adsorbed vinyl acetate removed from the carbon by the $CS_2$-acetone) can vary from one laboratory to another and from one batch of carbon to another. The desorption efficiency may vary with the quantity of vinyl acetate adsorbed on the carbon.

(b) Remove the Caplug from the same lot to be used for sampling. Remove the glass wool retainers. Transfer the content of the primary section (150 mg) into respective desorption efficiency test tubes.

(c) Remove the glass wool separators from the charcoal tubes and fill 2 additional desorption efficiency test tubes by combining the backup section (75 mg) from two carbon tubes into one desorption tube.

(d) Cap the open end of the desorption test tubes with Parafilm. (Trademark of American Can Company, DIXIE/MARATHON Division, Greenwich, Connecticut, for paraffin wax.)

(e) Pipet 0.5 ml of vinyl acetate into a 10-ml volumetric flask containing 7 to 8 ml of hexane. Dilute to the mark with additional hexane.

(f) By means of a 10-$\mu$l syringe, inject 2-$\mu$l of this solution into each of four desorption tubes containing the carbon. Insert the needle of the microliter syringe through the Parafilm and inject directly into the carbon, moving the needle at intervals to spread the solvent on the carbon. These tubes contain 92.8 $\mu$g of vinyl acetate.

(g) Into each of the 2 remaining tubes, inject 2-$\mu$l of hexane. Reserve these tubes as blanks. (Make sure the mircroliter syringe is thoroughly clean before injecting the hexane. If the same syringe from paragraph (f) is used, a memory effect could cause a false blank.)

(h) Reseal the tubes with an additional piece of Parafilm. Allow the tubes to stand overnight before analyzing to assure complete adsorption of the organic material onto the carbon.

(i) Follow the procedure as outlined in the Analytical Procedure, paragraphs (c) through (m) for desorption and analysis of the carbon, including the blank tubes.

(j) Calculate the desorption efficiency as follows:

$$\frac{\text{Average weight } (\mu g) \text{ recovered} - \text{Blank}, \mu g}{\text{weight } (\mu g) \text{ added}} = D.E.$$

CALCULATIONS $$\frac{(A - B) \times 24.45 \times 760 \times (T + 273°)}{D.E. \times L \times 86.09 \times P \times 298} = \begin{array}{l}\text{vinyl acetate,}\\ \text{ppm by volume at}\\ \text{25° C. and 760 mm Hg}\end{array}$$

A = micrograms of vinyl acetate per ml in sample activated carbon tube read from calibration curve.

B = micrograms of vinyl acetate on the blank carbon tube.

D.E. = desorption efficiency (j).

L = total volume of air sampled in liters.

P = pressure (mm Hg) of air sampled.

T = temperature (°C.) of air sampled.

Although the invention has been described in its preferred form with a certain degree of particularity, it will be recognized by those skilled in the art that variations may be made without departing from the scope and the spirit of the invention.

What is claimed is:

1. A method of measuring the amount of vinyl acetate monomer in an ambient air atmosphere which comprises the series of steps of:
(A) contacting a measured volume of ambient air containing vinyl acetate monomer vapor with drying means thereby freeing said measured volume of ambient air of water vapor;
(B) contacting the said water vapor-freed measured volume of ambient air with vinyl acetate adsorbing means, said adsorbing means containing an inhibitor for vinyl acetate polymerizaton thereby separating the vinyl acetate monomer in the measured volume of ambient air from said ambient air;
(C) desorbing the adsorbed vinyl acetate monomer from said vinyl acetate adsorbing means; and
(D) measuring the amount of desorbed vinyl acetate with analytical means for assaying vinyl acetate.

2. Method claimed in claim 1 wherein the drying means is anhydrous calcium sulfate.

3. Method claimed in claim 1 wherein the drying means is a crystalline zeolite of the molecular sieve type.

4. Method claimed in claim 1 wherein the adsorbing means is activated carbon.

5. Method claimed in claim 1 wherein the adsorbing means is bead activated carbon.

6. Method claimed in claim 1 wherein the polymerization inhibitor is hydroquinone.

7. Method claimed in claim 1 wherein the vinyl acetate monomer containing ambient air atmosphere is contacted with the drying means and adsorbing means at a rate of about 15 to about 90 liters of air per 2 grams of drying agent and per 150 mg. of adsorbent at a flow rate of 50–1000 cc/min.

* * * * *